United States Patent [19]

Sirover

[11] Patent Number: 4,818,685

[45] Date of Patent: Apr. 4, 1989

[54] METHOD AND KIT FOR DIAGNOSING BLOOM'S SYNDROME

[75] Inventor: Michael A. Sirover, Richboro, Pa.

[73] Assignee: Temple University of the Commonwealth Systems of Higher Education, Philadelphia, Pa.

[21] Appl. No.: 13,745

[22] Filed: Feb. 12, 1987

[51] Int. Cl.$^4$ .................. G01N 33/53; G01N 33/535; G01N 33/577

[52] U.S. Cl. .......................................... 435/7; 435/4; 435/172.2; 435/240.27; 435/810; 436/512; 436/548; 436/811; 935/110

[58] Field of Search ............... 436/508, 548, 813, 512, 436/548, 811; 435/4, 6, 7, 172.2, 240.27, 810; 935/110

[56] References Cited

U.S. PATENT DOCUMENTS 4,442,203  4/1984  Varsharsky .................. 435/4 X
4,699,877  10/1987 Cline ........................... 436/508 X

FOREIGN PATENT DOCUMENTS 0057553  8/1982  European Pat. Off. .

OTHER PUBLICATIONS

Chemical Abstracts, 104:127689c (1986).

Y. Yamamoto et al., "Abnormal Regulation of Uracil-DNA Glycosylase Induction During Cell Cycle and Cell Passage in Bloom's Syndrome Fibroblasts", *Carcinogenesis*, vol. 7, No. 2, pp. 305-310 (1986).

P. K. Gupta et al., "Altered Temporal Expression of DNA Repair in Hypermutable Bloom's Syndrome Cells", *Proc. Natl. Acad. Sci. U.S.A.*, vol. 81, pp. 757-761, (Feb. 1984).

Arenaz et al., "Isolation and Characterization of Monoclonal Antibodies Directed Against the DNA Repair Enzyme Uracil DNA Glycosylase from Human Placenta", *Proc. Natl. Acad. Sci. U.S.A.*, 80:5822-5826 (1983).

*Primary Examiner*—Sidney Marantz
*Attorney, Agent, or Firm*—Seidel, Gonda, Lavorgna & Monaco

[57] ABSTRACT

A method and kit for diagnosing Bloom's syndrome are provided relying on specific monoclonal antibodies, such as ATCC HB-9311, which recognize the base excision repair pathway enzyme uracil DNA glycosylase from normal healthy individuals and individuals afflicted with genetic syndromes, but fails to recognize uracil DNA glycosylase from individuals afflicted with Bloom's Syndrome.

16 Claims, 4 Drawing Sheets

METHOD AND KIT FOR DIAGNOSING BLOOM'S SYNDROME

FIELD OF THE INVENTION

The invention relates to a simple and rapid method for diagnosing Bloom's syndrome using monoclonal antibodies. The invention also relates to a kit for practicing the method.

REFERENCE TO GOVERNMENT GRANT

The invention described herein was supported by National Institutes of Health Grants CA-29414 and CA-12227. The United States government has certain rights in the invention.

BACKGROUND OF THE INVENTION

Bloom's syndrome cells are characterized by abnormally high spontaneous mutation rates. It has been reported that Bloom's syndrome cells are hypermutable with spontaneous mutation frequencies five- to ten-fold higher than normal cells. Bloom's syndrome cells are singularly susceptible to transformation by DNA transfection. Individuals with Bloom's syndrome have an increased rate of neoplasia, infertility, immune deficiency and infection.

Bloom's syndrome is characterized by a high level of chromosomal aberration, particularly sister chromatid exchanges. It is, along with Fanconi's anemia, and ataxia telangiectasia, one of three genetic diseases in which unrepaired chromosomal breakage occurs with several times the frequency observed in normal individuals.

Bloom's syndrome is inherited as an autosomal recessive condition. The Bloom's syndrome gene appears to be widespread in the population, with cases reported in Ashkenazi-Jewish, Japanese, American Black, Western European Christian, and non-Jewish semitic (Mohammedan) ethnic groups.

In addition to unrepaired chromosome breakage, other cytogenetic abnormalities are present with an abnormally high frequency, such as chromosomal rearrangements, deletions and "fusion fissures". The latter appears to result from a break in a single chromatid in each of two chromosomes.

Clinically, Bloom's syndrome is associated with congenital malformations and a predisposition to malignancy. The disease is characterized by low birth weight, not due to prematurity, and severe, generalized growth retardation. Bloom's syndrome presents a telangiectatic erythema which primarily affects facial areas, and a sun-sensitivity which can initiate or accentuate the facial lesions.

There are no methods for specific diagnosis of Bloom's syndrome at the cellular, molecular or biochemical level. The sole means for diagnosis is a clinical evaluation by a physician as symptoms became apparent. However, even in areas where excellent health care is available, diagnosis may be difficult due to the diversity of symptoms and the degree of their severity. Diagnosis of Bloom's syndrome may be impeded where health care is unavailable.

What is needed is a simple, reliable biochemical/immunological test for diagnosing Bloom's syndrome. In particular, there is a need to identify children afflicted with Bloom's syndrome early after birth but prior to appearance of clinical symptoms, and in utero at an early stage of gestation. Since Bloom's syndrome patients are cancer-prone, diagnosis would permit careful monitoring for detection of tumors at an early stage when the cancer is most responsive to treatment.

Recent studies have demonstrated that eucaryotic cells actively regulate DNA repair pathways during the defined temporal pattern of gene expression observed during cell proliferation. In comparison to quiescent cells, proliferating cells exhibit increased levels of DNA repair enzyme, increased excision repair synthesis, and faster removal of DNA lesions. In serum-synchronized normal human cells, DNA repair pathways are enhanced prior to DNA synthesis and are decreased during S phase.

No difference has been observed in the excision of DNA adducts, or in the level of DNA repair enzymes, in non-growing Bloom's syndrome cells. However, in spontaneously hypermutable Bloom's syndrome cells, there is a failure to enhance DNA repair pathways prior to DNA replication. Instead, both nucleotide excision repair synthesis and base excision repair synthesis are enhanced coordinate with DNA replication.

The most important DNA repair pathways in humans depend on the excision of an altered residue or group. The group of enzymes known as DNA glycosylases catalyze the cleavage of base-sugar bonds in DNA. They act only on altered or damaged nucleotide residues.

Uracil DNA glycosylase functions as an initial enzyme in the base excision repair pathway to remove uracil residues from DNA by cleavage of the base-sugar glycosyl linkage producing an apyrimidinic site in DNA. Uracil may arise in DNA through the mutagenic deamination of cytidine, or through incorporation of deoxyuridine 5'-monophosphate during DNA replication. Human uracil DNA glycosylase has been extensively purified and characterized. It has a molecular weight of about 37,000 daltons. Uracil DNA glycosylase may be measured by quantitation of in vitro enzymatic activity or by enzymelinked immunosorbent assay ("ELISA") with anti-human-uracil DNA glycosylase monoclonal antibodies. Arenaz, P. and M. A. Sirover, *Proc. Natl. Acad. Sci. USA*, 80: 5822–5826 (1983).

Hereinafter, "UDG" shall mean the human base excision-repair enzyme uracil DNA glycosylase.

"Bloom's syndrome UDG" shall mean any genetic variant of UDG characteristic of Bloom's syndrome.

"Anti-human UDG monoclonal antibody" shall mean a monoclonal antibody which recognizes normal human UDG.

SUMMARY OF THE INVENTION

A method of diagnosing Bloom's syndrome is provided. A sample containing human UDG is contacted with an anti-human UDG monoclonal antibody which does not recognize Bloom's syndrome UDG. The sample is then assayed for binding of UDG to the monoclonal antibody. Preferably, the same sample or other aliquot thereof is contacted with a second anti-human UDG monoclonal antibody which recognizes both normal UDG and Bloom's syndrome UDG as a control. The control sample is then assayed for binding or UDG by the second monoclonal antibody.

A kit for practicing the method of diagnosing Bloom's syndrome is also provided. The kit contains a carrier for receiving one or more container means. A first container means comprises a first detectably-labeled anti-human UDG monoclonal antibody which does not recognize Bloom's syndrome UDG. A second container means comprises a second detectably-labeled anti-human UDG monoclonal antibody which recognizes both normal UDG and Bloom's syndrome UDG. Alternatively, the kit may contain the first and second anti-human UDG monoclonal antibodies in unlabled form. A third container means would therefore comprise a detectably-labeled secondary antibody or F(ab) fragment capable of binding either the first or second monoclonal antibodies.

DETAILED DESCRIPTION OF THE INVENTION

Figure 1:
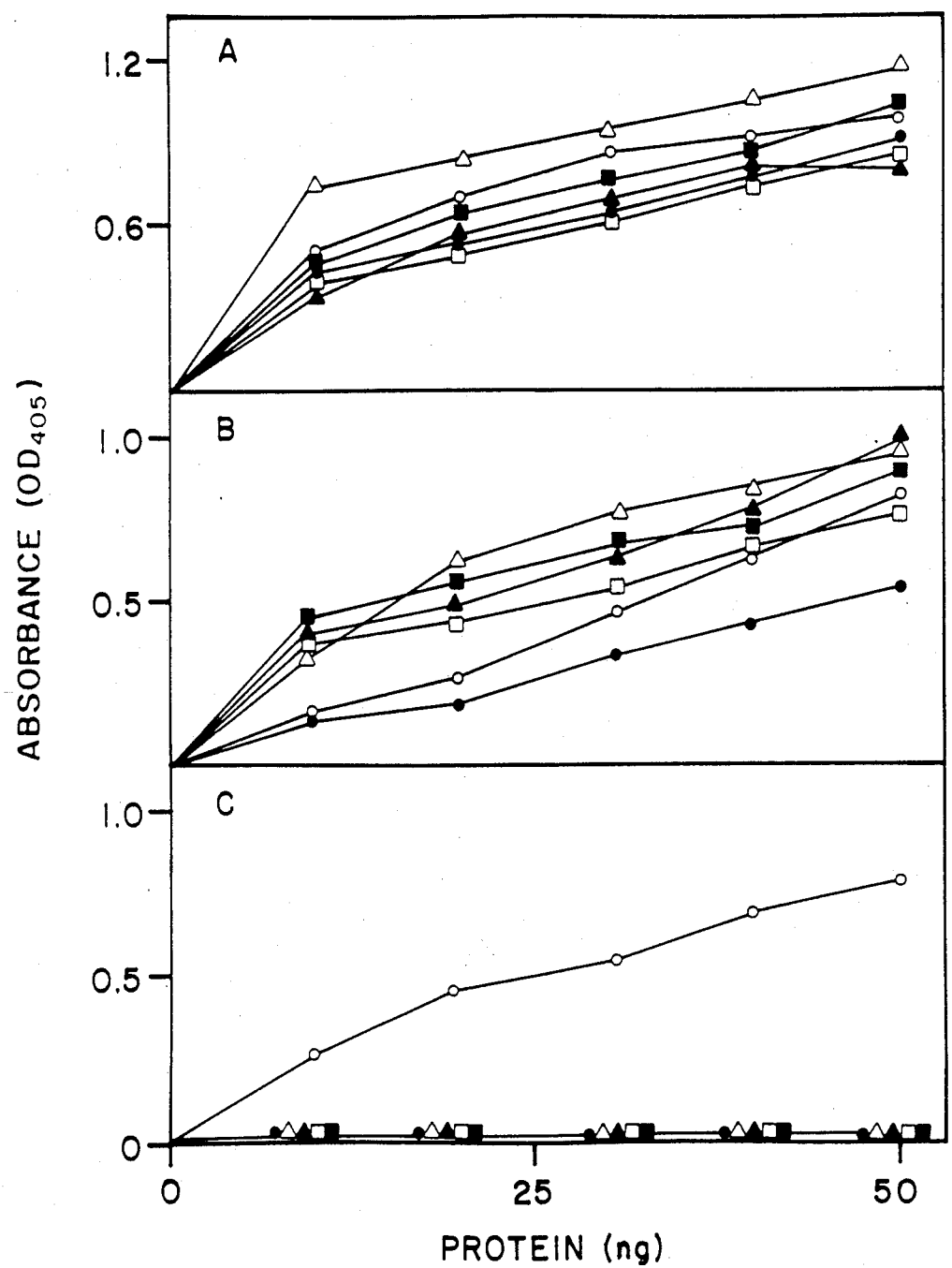
FIG. 1 is a plot of an ELISA of the reaction between monoclonal antibodies 37.04.12 (FIG. 1A), 42.08.07 (FIG. 1B), and 40.10.09 (FIG. 1C) with
  Normal human cells (CRL 1222 (hollow circles);
  "Bloom's syndrome strain GM 1492 (solid circles)"
  Bloom's syndrome strain GM 2548 (hollow triangles);
  Bloom's syndrome strain GM 3402 (solid triangles);
  Bloom's syndrome strain GM 3498 (hollow rectangles); and
  Bloom's syndrome strain GM 3510 (solid rectangles).

In Bloom's syndrome cells, uracil DNA glycosylase is induced coordinate with DNA synthesis. This suggests that the altered temporal regulation of the uracil DNA glycosylase gene in Bloom's syndrome cells is accompanied by a structural alteration in the Bloom's syndrome uracil DNA glycosylase protein. The invention is based upon the discovery that certain anti-UDG monoclonal antibodies are specific for normal UDG and do not recognize UDG from individuals afflicted with Bloom's syndrome. Immunoreactivity with Bloom's syndrome UDG is restored following denaturation of the enzyme, thereby further suggesting that Bloom's syndrome is characterized by a structural alternation in the UDG molecule which, at least in the native form of the molecule, masks the antigen site for anti-UDG monoclonal antibodies. The discovery makes possible a diagnostic test for Bloom's syndrome relying on monoclonal antibodies.

Anti-UDG monoclonal antibodies, such as antibody 40.10.09 (described below), which fail to recognize Bloom's syndrome UDG are used according to the present invention in a method of detecting Bloom's syndrome. A UDG-containing sample is contacted with the monoclonal antibody. The sample is then assayed for binding of UDG to the antibody by standard immunoassay.

The sample may be taken from any suitable UDG-containing cells such as blood cells, fibroblasts, etc, or from blood samples directly without centrifugation or disruption. The sample may be prepared by collecting cells by centrifugation, disrupting the cells by, for example, sonication, and removing the cell debris, thus resulting in a cell-free extract. According to one embodiment of the invention, the sample may take the form of a cell-free extract prepared by pelleting cells at $800 \times g$ for 15 minutes, sonicating the pellet in 1.0 ml of buffer (20 mM Tris.HCl, pH 7.9/1 mM dithiothreitol) at 60 watts for 30 seconds in an ice bath, and recovering the supernatant after centrifugation of the sonicate at $800 \times g$ for 10 minutes at 4° C.

The sample is assayed for possible binding of UDG. Any suitable antibody binding assay may be used, provided it does not result in substantial denaturation of the UDG. Immunoreactivity with Bloom's syndrome UDG is restored upon denaturation of the enzyme, possibly resulting in a false negative reading for Bloom's syndrome. Therefore, antibody binding assays which cause, or risk causing, substantial denaturation of the antigen, such as immunoblotting and immunoprecipitation, should not be employed.

The assay is preferably conducted against a control comprising a second monoclonal antibody, such as antibody 42.08.07 (described below), which recognizes both normal UDG and Bloom's syndrome UDG. The specimen may be thus assayed for binding of UDG by the second monoclonal antibody. The test and control assays are most advantageously conducted side-by-side, for instance by applying the anti-Bloom's syndrome UDG-negative monoclonal antibody to one well of a microtiter plate and the anti-Bloom's syndrome UDG-positive antibody to a neighboring well. A positive assay in the control well ensures that there is sufficient UDG in the specimen for assay, and ensures that the absence of immunoreactivity between the sample and the anti-Bloom's syndrome UDG-negative antibody is attributable to the variant Bloom's syndrome UDG, not artifact.

As yet a further control, the anti-Bloom's syndrome UDG-negative monoclonal antibody may be assayed for binding with normal UDG, thus ensuring the antibody's functional integrity. A positive binding assay indicates that the antibody is functional.

The preferred antibody binding assays are those which involve attaching the UDG antigen or anti-UDG monoclonal antibodies to an insoluble support, although other assays may be employed. When the antibody or antigen is coupled to an insoluble support, the bound complex can readily be separated and detected. A wide variety of solid phase supports have been described, such as dextran, cellulose, polystyrene, polypropylene and the walls of glass tubes or slides. Plastic surfaces are adsorptive. Exposing the surface to the appropriate dilution of protein (antigen or monoclonal antibody) will lead to attachment. Covalent bonding to the surface can be obtained by incorporation of cross-linking agents into the antibody or antigen surface used for coating.

The monoclonal antibodies may be detectably labeled with a label which is affixed to the antibodies. The label is detected by some physical or chemical means. Such labels include radio-labes; chromophoric labels, such as fluorescent, ultraviolet-absorbing or light-absorbing labels; enzyme labels; etc. In the ELISA assay, the label is an enzyme, e.g. alkaline phosphatase, which cleaves a chromogenic substrate to release a chromophoric cleavage product. In the case of alkaline phosphatase, the presence of antigen is signalled by hydrolysis of the substrate p-nitrophenylphosphate, which releases the yellow-colored compound p-nitrophenol.

More conveniently, the label is affixed to a secondary monoclonal or polyclonal antibody or F(ab) fragment which binds the primary UDG-specific monoclonal antibodies. For this double antibody technique, the secondary antibody may advantageously comprise, for example, rabbit-, sheep-, or goat-anti-mouse IgG. The double antibody technique is preferred.

The preferred assay means is an ELISA. While a radioimmunoassay could be used as part of an ELISA, this would require radio-labelling of homogeneous UDG, which is expensive and could result in destruction of antigenic cites on the protein molecule.

The monoclonal antibodies employed in the practice of the present invention may be prepared according to the method of Arenaz and Sirover, *Proc. Natl. Acad. Sci. USA:* 80 5822–5826 (1983). Briefly, mice are immunized with purified human placental UDG. BALB/c mice are preferred, although other strains may be used. The immunization schedule and concentration of immunogen administered should be such as to produce useful quantities of suitably primed splenocytes.

Upon completion of the immunization regimen more completely described below, the mice are sacrificed and their spleens are removed. A suspension of the splenocytes in a suitable medium is then prepared. The protocols for in vitro cell suspension are well established.

The spleen cells are fused with mouse myeloma cells by means of a fusion promoter. Fusion is advantageously accomplished according to a modification of the procedure described in R. H. Kennett "Fusion Protocols: Fusion By Centrifugation Of Cells Suspended In Polyethylene Glycol" in *Monoclonal Antibodies: Hybridomas: A New Dimension In Biological Analyses*, (Kennett. R. H., McKearn, T. J. and Bechtol, K. B., eds.), Plenum Press, New York and London, 365–367 (1980). Other fusion techniques known to those skilled in the art may be employed. The preferred fusion promoter is polyethylene glycol, most preferably polyethylene glycol of molecular weight 1,000. Other promoters may be used. The mouse myeloma cell line is preferably one of the "drug-resistant" types to enable selection of hybrids. The most frequently used class of myelomas are the 8-azaguanine-resistant cell lines, which are widely known and available. These lines lack the enzyme hypoxanthine guanine phosphoribosyl transferase and therefore do not survive in "HAT" (hypoxanthine aminopterin-thymidine) medium.

A mixture of unfused myeloma cells, unfused spleen cells and fused cells are distributed for culturing in separate compartments (e.g., the wells of a 96-well microtiter plate) in a selective medium in which the unfused myeloma cells will not survive. Distribution of the cells may be by resuspension in a volume of diluent which is statistically calculated to isolate a desired number of cells per compartment.

When HAT is used as the medium, unfused 8-azaguanine-resistant myeloma cells will not grow. Unfused spleen cells will normally die after a few days, since they are non-malignant.

The supernatant in each container or compartment having hybrid cell growth is screened and evaluated for the presence of antibody to UDG. Any suitable antibody-binding detection method may be used. An enzyme-linked immunosorbent assay is preferred. After selection and cloning, monoclonal antibodies to UDG may be produced by in vitro culturing of the hybridoma or by in vivo peritoneal exudate induction in mice. The first method will yield monoclonal antibody of high purity. Where concentrations of antibody larger than those obtained by in vitro culturing of hybridomas are required, the subject hybridomas may be injected into the peritoneal cavity of pristane-primed mice. An injection containing $1-2\times 10^7$ hybridoma cells is sufficient for this purpose.

The resulting anti-UDG monoclonal antibodies are then screened to isolate those species which fail to recognize Bloom's syndrome UDG. Bloom's syndrome UDG required for this purpose may be purified from available Bloom's syndrome cell strains such as the fibroblast lines GM 2548 and GM 1492, Human Genetic Cell Repository, Camden, N.J. Anti-UDG monoclonal antibodies may be most advantageously screened for the absence of immunoreactivity with Bloom's syndrome UDG by using an ELISA.

The monoclonal antibodies used in the practice of the present invention (both anti-Bloom's syndrome UDG positive and anti-Bloom's syndrome UDG negative species), normal UDG, and Bloom's syndrome UDG, may be prepared according to the following methods.

PREPARATION OF THE IMMUNOGEN

Human placental UDG may be prepared according to the technique of Arenaz and Sirover, *Proc. Natl. Acad. Sci. USA:* 80 5822–5826 (1983). Freshly-obtained human placenta is washed in 0.15M KCl and dissected free of its connective tissue. The remaining tissue is homogenized six times for 1 minute each time in a Waring blender at 4° C. in Buffer I (20 mM Tris.HCl, pH 7.9/1 mM dithiothreitol). The suspension is centrifuged at 20,000×g for 20 minutes and the cell pellet is discarded. In this procedure, the mitochondria is pelleted and the mitochondrial glycosylase, which accounts for only 5–10% of the total glycosylase activity, is removed. The supernatant is adjusted to 20% (vol/vol) glycerol and adsorbed to a DEAE-cellulose column previously equilibrated with Buffer II (20 mM Tris.HCl, pH 7.9/1 mM dithiothreitol/20% glycerol). The column is washed with 1 column volume of Buffer II to elute the enzyme. Peak fractions of glycosylase activity are pooled and adsorbed directly onto a phosphocellulose column. The column is washed with 1 vol of Buffer II followed by a 0–1 M KCl gradient in Buffer II. The peak fractions from the phosphocellulose column are pooled and dialyzed twice in 3.5 liters of Buffer III (10 mM potassium phosphate, pH 6.5/2 mM $K_2$EDTA/0.5 mM dithiothreitol/20% glycerol). The dialysate is absorbed onto a hydroxylapatite column and eluted with a gradient of 10–300 mM potassium phosphate in Buffer III.

IMMUNIZATION AND PREPARATION OF HYDRIDOMAS

UDG purified from hydroxylapatite column chromatography as above is dialyzed against 4 liters of phosphate-buffered saline. BALB/c mice, age 6–8 weeks, are injected intraperitoneally with the UDG (75 micrograms per mouse) in phosphate-buffered saline mixed 1:1 with complete Freund's adjuvant. A booster of 15 micrograms per mouse, mixed 1:1 with incomplete Freund's adjuvant, is given intraperitoneally 3 weeks later. After an additional 3 weeks, a final booster of 11.5 micrograms per mouse, in phosphate-buffered saline, is given intraveneously. The mice are sacrificed 3 days later and their spleens are removed.

Mouse myeloma lines SP2/0 and P3×63 Ag8.653 (V653) (available as GM3369 and GM3570, respectively, from the Human Genetic Cell Repository, Camden, NJ) are routinely maintained in midlogarithmic phase in Dulbecco's modified Eagle's medium (DME sodium) supplemented with 10% fetal bovine serum, 2 mM L-glutamine, and gentamycin at 1 micro-gram/ml. Fusion is accomplished by a modification of the procedure described by Kennett, *Monoclonal Antibodies*, p. 365–367 (1980). The cells from each spleen are separated into two equal aliquots ($5-6 \times 10^7$ cells per aliquot) and mixed with either SP2/0 or V653 ($5-6 \times 10^6$ cells) in the presence of polyethylene glycol (MW=1,000) for 1.5 minutes at 37° C. The cells are centrifuged at $250 \times g$ for 6 minutes and suspended in selective medium containing hypoxanthine, thymidine, and aminopterin and cultured at 37° C. in humidified 8% $CO_2$/92% air.

Spent culture fluid from growing cultures is assayed for anti-UDG activity by enzyme-linked immunosorbent assay (ELISA) according to Engvall, E., *Methods Enzymol.*, 70: 419–439 (1980). Microtiter plates are coated with UDG by incubating each well with 100 microliters of glycosylase (100 micrograms/ml) in phosphate-buffered saline at pH 7.0 for 2 hr at 37° C. in a humidified atmosphere. The plates are washed twice with phosphate-buffered saline containing 1% bovine serum albumin, then incubated at 37° C. for 20 minutes with 100 microliters of phosphate-buffered saline/1% bovine serum albumin per well. The plates are washed twice with phosphate-buffered saline and 50 microliters of spent culture fluid are added to each well (two wells per clone). The plates are incubated for 2 hours at 37° C. in a humidified atmosphere. Each plate is washed twice with washing buffer containing 10 mM Tris.HCl, pH 7.4, and Tween 20. To each well is added 50 microliters of a 1:250 dilution of alkaline phosphatase-conjugated F(ab')$_2$ fragments of sheep antiserum to mouse IgG (New England Nuclear) and incubated for 2 hours at 37° C. Plates are washed as above in washing buffer and washed twice in distilled water, and 50 microliters of p-nitrophenyl phosphate are added in each well. After 14–16 hours at room temperature, plates are checked for positive wells. Supernatants from a previously isolated and spontaneous hybridoma clone are used as a negative control. Hybridomas scored as positive in the ELISA are cloned by limit dilution in DME medium with hypoxanthine and thymidine. Positive clones are recloned by limit dilution and tested again for anti-UDG activity by immunoprecipitation. Hybridomas that are positive in ELISA and immunoprecipitate glycosylase activity are grown for collection of spent fluid and for ascites tumor production. To produce ascites tumors, $1-2 \times 10^7$ hybridoma cells are injected intraperitoneally into pristane-primed mice.

Clones producing monoclonal antibodies which fail to recognize Bloom's syndrome UDG are then selected from among clones producing antibody testing positive for anti-UDG activity. Bloom's syndrome UDG for this screening may be prepared following the above procedure for purifying normal UDG, "Preparation of the Immunogen", but substituting an appropriate Bloom's syndrome UDG source, e.g., fibroblast line GM1492, for human placenta. More conveniently, screening may be carried out using a crude source of Bloom's syndrome UDG antigen, such as cell free extract prepared by pelleting cells at $800 \times g$ for 15 minutes, sonicating the pellet in 1.0 ml of buffer (20 mM Tris.HCl, pH 7.9/1 mM dithiothreitol) at 60 watts for 30 seconds in an ice bath, and recovering the supernatant after centrifugation of the sonicate at $800 \times g$ for 10 minutes at 4° C. Even more conveniently, Bloom's syndrome UDG-containing cells such as blood cell fibroblasts, or blood samples, may be used directly without centrifugation or disruption for purposes of screening.

Screening of the anti-UDG positive clones against Bloom's syndrome UDG is most advantageously performed by the same ELISA technique provided in "Immunization and Preparation of Hybridomas", above, substituting Bloom's syndrome UDG for normal UDG.

Ninety-two clones exhibiting exceptional anti-UDG activity were prepared. Four such clones, designated PM 16.11.08, PM 37.04.12, PM 40.10.09 and PM 42.08.07 were selected for further study. Clone PM 40.10.09 failed to recognize Bloom's syndrome UDG as determined by ELISA.

Clone PM 40.10.09 was deposited in the American Type Culture Collection, 12301 Parklawn Drive, Rockville, Md. 20852 on Jan. 20, 1987 and assigned ATCC accession number HB-9311. Clones PM 37.04.12 and 42.08.07, deposited on Jan. 20 and 21, respectively, were assigned accession numbers HB-9312 and HB-9313.

To determine the specificity of the lack of immunoreactivity between Bloom's syndrome UDG and antibody PM 40.10.09, purified UDG was prepared from normal human cells (CRL 1222) and from five separate Bloom's syndrome strains. (GM 1492, GM 2548, GM 3402, GM 3498 and GM 3510).

Each UDG was assayed for antibody binding by ELISA using three separate anti-UDG monoclonal antibodies. As shown in FIG. 1, normal UDG (hollow circle data points) was recognized in a concentration-dependent manner by each of the three monoclonal antibodies 37.04.12 (FIG. 1A), 42.08.07 (FIG. 1B) and 40.10.09 (FIG. 1C). Similarly, UDG from each of the five separate Bloom's syndrome cell strains, GM 1492 (solid circles), GM 2548 (hollow triangles), GM 3402 (solid triangles), GM 3498 (hollow rectangles) and GM 3510 (solid rectangles), was recognized by monoclonal antibodies 37.04.12 and 42.08.07. However, UDG from the five Bloom's syndrome strains was not immunoreactive with monoclonal antibody 40.10.09. See FIG. 1C.

Figure 2:
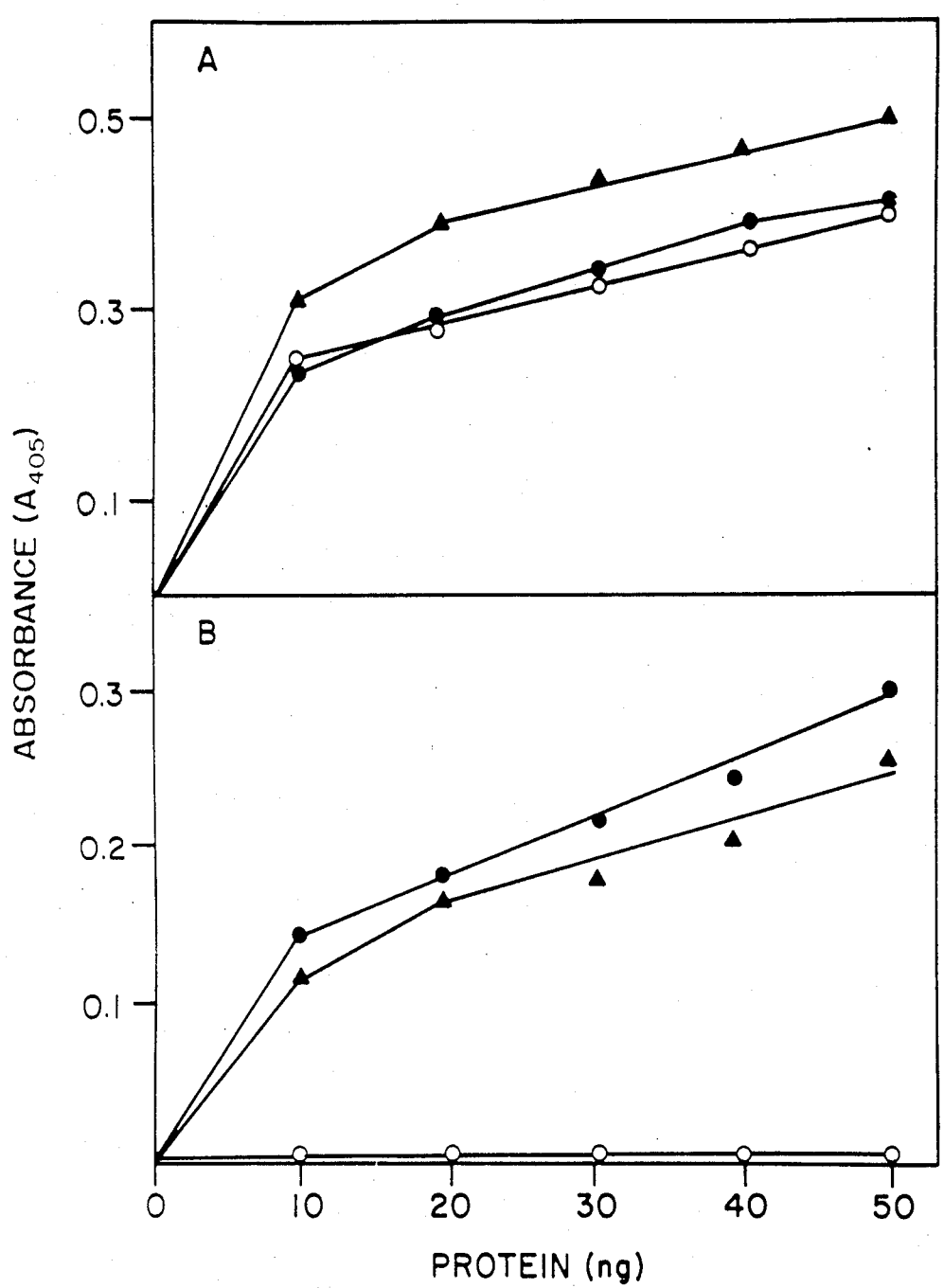
FIG. 2 is a plot of an ELISA of the reaction between (A) antibody 42.08.07 and (B) antibody 40.10.09, and crude cell extracts. Protein on the X axis represents nanogram amounts of normal human cell extract (solid circles), GM2548 Bloom's syndrome cell extract (hollow circles), and total protein in a 1:1 mixture of normal human cell extract protein and Bloom's syndrome cell extract protein (solid triangles).

Mixing experiments were performed to determine whether the failure of antibody 40.10.09 to recognize Bloom's syndrome UDG was due to the presence of inhibitor in the Bloom's syndrome extract. Equal concentrations of normal human and Bloom's syndrome cell-free extract were mixed in an ELISA with antibody 42.08.07. As shown in FIG. 2A, the mixture had a greater amount of reactivity with antibody 42.08.07 than observed with equal concentrations of each extract tested individually. Antibody 40.10.09 was tested for reactivity against the same mixture of normal human and Bloom's syndrome cell-free extracts. No drastic inhibition was observed. See FIG. 2B.

Figure 3:
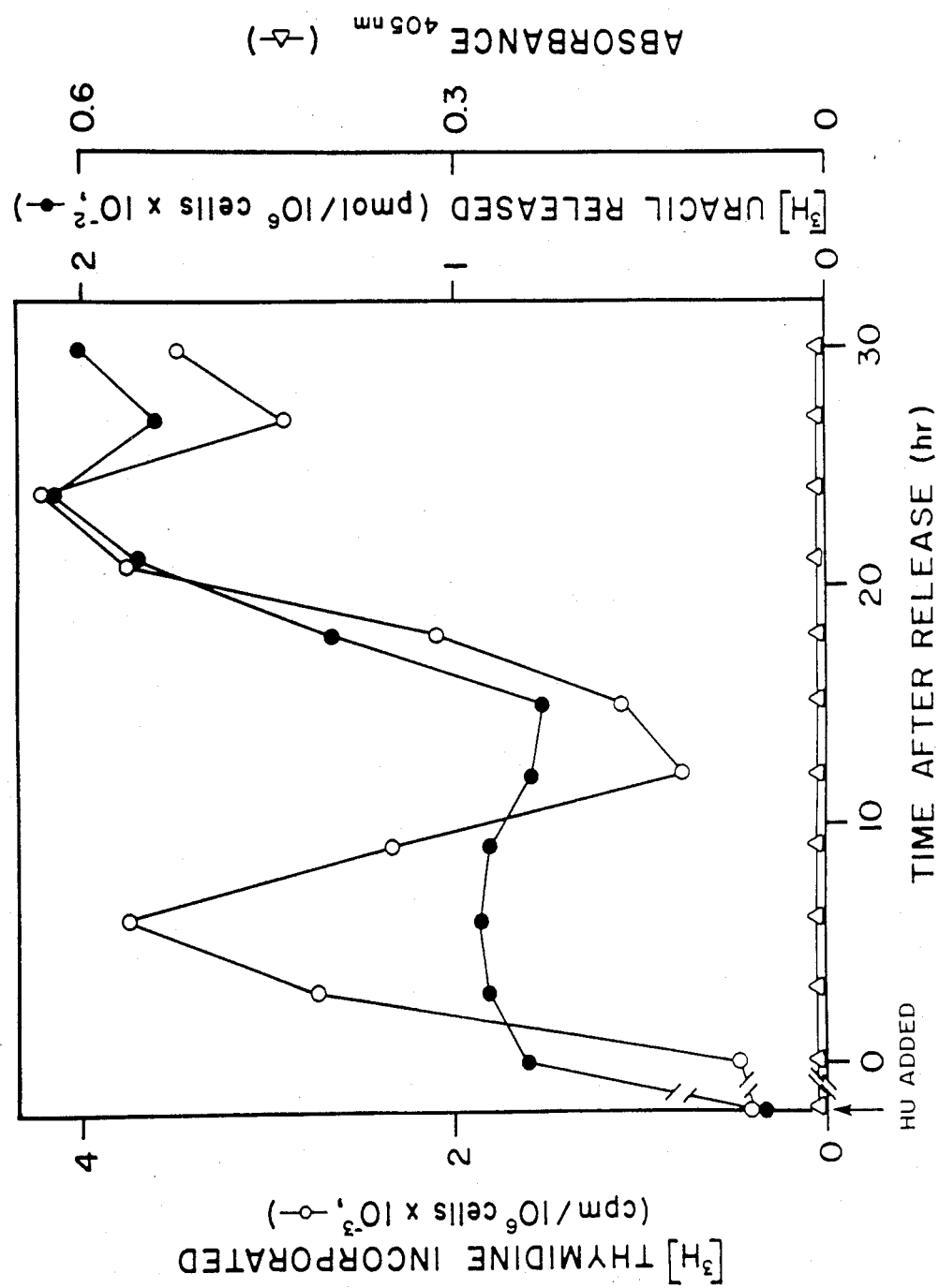
FIG. 3 is a plot of an ELISA of the reaction between antibody 40.10.09 and extracts from Bloom's syndrome cells (strain GM 2548) during various stages of cell proliferation (hollow triangles).

To eliminate the possibility that a UDG isoenzyme recognized by antibody 40.10.09 is expressed in proliferating Bloom's syndrome cells, UDG-containing cell extracts were prepared from strain GM 2548 during various intervals of cell proliferation according to the method of Dehazya and Sirover, *Cancer Research* 46: 4756-3761 (1986). As shown in FIG. 3, antibody 40.10.09 failed to recognize Bloom's syndrome UDG (hollow triangles) produced during various intervals of cell proliferation, spanning the peak intervals of induction of DNA synthesis (hollow circles) and induction of UDG synthesis (solid circles).

The immunoreactivity of the monoclonal antibodies to denatured UDG was then examined. Heating normal UDG for ten minutes at 100° C. did not diminish immunoreactivity with either monoclonal antibody 40.10.09 or 42.08.07. See FIG. 4A. Similarly, the normal human enzyme was immunoreactive even after heating in the presence of SDS. See FIG. 4B. (However, there was a demonstrable decrease in absorbence of approximately 70% in the ELISA assay.)

Figure 4:
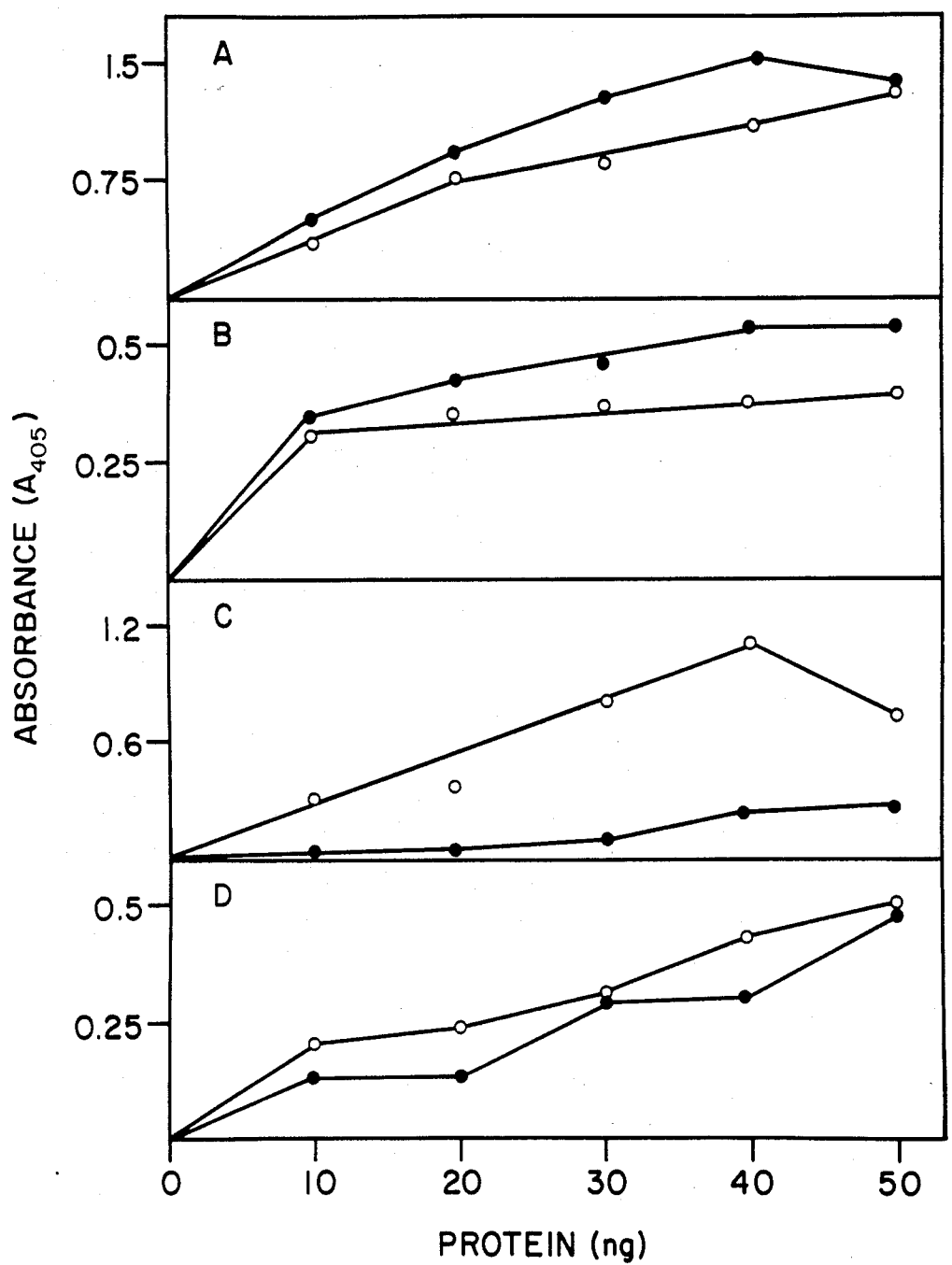
FIG. 4 is a plot of an ELISA of the reaction between antibodies 42.08.07 (hollow circles) and 40.10.09 (solid circles), and the cell extracts used in FIG. 1, which were treated as follows before the ELISA to provide:
  (A) Normal UDG, heat-denatured in the absence of SDS;
  (B) normal UDG, denatured in the presence of SDS;
  (C) GM2548 Bloom's syndrome UDG, denatured in the absence of SDS; and
  (D) GM2548 Bloom's syndrome UDG, heat-denatured in the presence of SDS.
Figure 3:
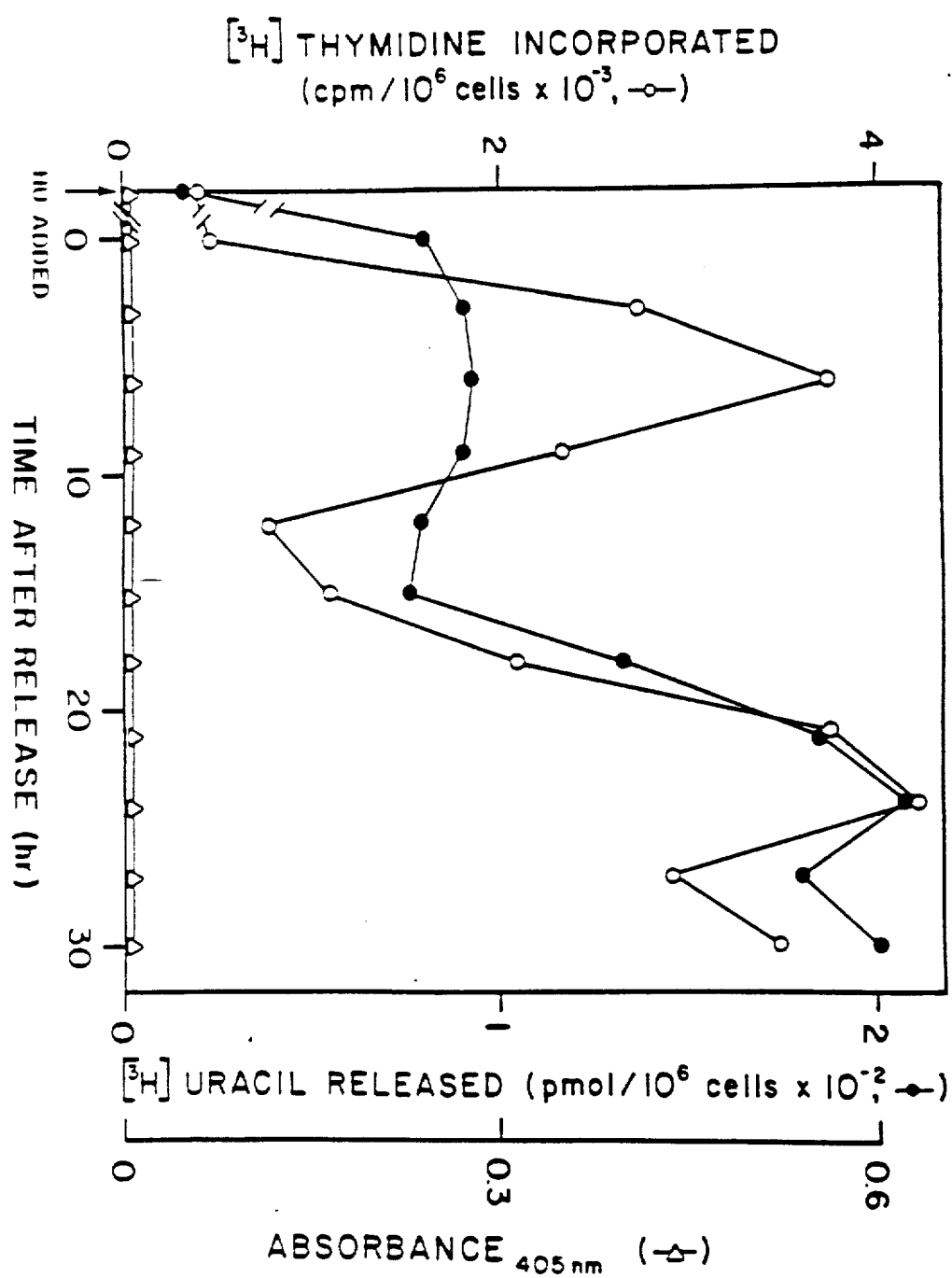

As shown in FIG. 4C, immunoreactivity with Bloom's syndrome UDG was observed with antibody 42.08.07 even after heating in the absence of SDS. However, no recognition of Bloom's syndrome UDG was observed by low protein concentrations following the same heat treatment. At higher protein concentrations, significant immunoreactivity of Bloom's syndrome UDG with antibody 40.10.09 was observed. Moreover, as shown in FIG. 4D, heating of Bloom'syndrome UDG in the presence of SDS resulted in a return of immunoreactivity with antibody 40.10.09 to a level equivalent to that observed with antibody 42.08.07.

The normal human and Bloom's syndrome cell-free extracts used in the above experiments were electrophoresed in SDS-PAGE and electroblotted into nitrocellulose paper under denaturing conditions. The electroblotted material was then reacted with monoclonal antibody 40.10.09. UDG was detected in both extracts. The antibody specifically reacted with a 37 kD cell protein in both extracts. The affinity of the antibody for each glycosylase is similar since the limit of detection of the enzyme by antibody 40.10.09 is between 1.1-5.5 micrograms for the normal human cell-free extract and between 2.2-10.9 micrograms for the Bloom's syndrome cell-free extract. The immunoblot analysis indicates that any difference between normal UDG and Bloom's syndrome UDG does not involve a change in the molecular weight of the protein.

These results demonstrate that there is a structural alteration in the Bloom's syndrome UDG protein which, in its native configuration, masks the antigenic determinant recognized by antibody 40.10.09. Denaturation of the protein by heat treatment or by SDS uncovers the determinant as demonstrated by ELISA assay and immunoblot analysis. Thus, the alteration of DNA repair gene expression observed in Bloom's syndrome cells is accompanied by an alteration in the structural gene for the UDG molecule.

The following is one example of the method of the present invention, relying on an ELISA technique to assay UDG-antibody binding.

EXAMPLE

UDG in 25 microliters of cell-free extract or purified enzyme fraction is absorbed into the well of a polyvinyl chloride microtitre plate (Costar). The plate is incubated for two hours at 37° C. and then further incubated at 4° C. for 48-72 hours to ensure maximum binding of the enzyme. The plate is washed two times with PBS plus 1 mg/ml BSA followed by the addition of 200 microliters of PBS plus 1 mg/ml BSA to each well to bind all remaining sites on the plate. After a 30 minute incubation, the plates are washed three times with PBS. To each well, 50 micrograms of monoclonal antibody 40.10.09 is added in a volume of 50 microliters. The plate is incubated for two hours at 37° C. in a humidified atmosphere and washed three times with washing buffer (10 mM Tris-HCl/pH 7.4/0.05% Tween 20). This is followed by the addition of 50 microliters of a 1:250 dilution of alkaline phosphatase-conjugated F(ab) fragment of sheep anti-serum to mouse IgG (New England Nuclear, Boston, MA) and incubation for an additional two hours at 37° C. The plate is washed as above in washing buffer followed by two washes in distilled water. Fifty microliters of p-nitrophenyl phosphate are added to each well. After 14-16 hours at room temperature, the reaction is stopped by the addition of 50 microliters of 0.5N NaOH, and the color may be quantitated by spectrophotometric analysis at 405 nm. A negative reaction is an indication that the UDG contained in the specimen is the Bloom's syndrome variant.

The specificity of Bloom's syndrome UDG in its failure to immunoreact with monoclonal antibody 40.10.09 was confirmed by assaying UDG from the five normal and nineteen human genetic variant cell lines in the Table for binding by antibody 40.10.09, 42.08.07 and 37.04.12. The assays were conducted according to the ELISA technique of the above Example. The results in the Table are expressed as the ratio of UDG immunoreactivity (as measured by absorbance at 405 nm) to the immunoreactivity of UDG from normal skin fibroblast strain CRL 1222. Ratios were determined at a minimum of four separate protein concentrations. Anti-human UDG monoclonal antibodies 37.04.12 and 42.08.07 recognized UDG from all cell sources in a concentration-dependent manner over a protein concentration range of 10 to 50 nanograms. Antibody 40.10.09 reacted with all such UDG over the same protein concentration range, except UDG from the five Bloom's syndrome fibroblasts GM 1492, 2548, 3402, 3498, and 3510 (all from the Human Genetic Cell Repository, Camden, NJ). Antibody 40.10.09 failed to recognize Bloom's syndrome UDG at a protein concentration of 10 to 50 nanograms, and at 10 micrograms (100 fold excess).

TABLE

Immunoreactivity Of Human Uracil DNA Glycosylases With Monoclonal Antibodies

| UDG Source | $A_{405}/A_{405-CRL\ 1222}$ | | |
|---|---|---|---|
| | 37.04.12 | 42.08.07 | 40.10.09 |
| Normal Human Cells | | | |
| Skin fibroblasts (CRL 1222)* | 1.00 | 1.00 | 1.00 |
| Human placenta | 0.92 ± 0.09 | 0.92 ± 0.19 | 0.90 ± 0.10 |
| Lymphocytes | 1.32 ± 0.23 | 1.04 ± 0.08 | 1.19 ± 0.26 |
| Lung fibroblasts (CCL 75)* | 1.02 ± 0.10 | 0.89 ± 0.16 | 0.94 ± 0.12 |
| Skin fibroblasts (GM 5879) | 0.98 ± 0.04 | 1.28 ± 0.07 | 0.91 ± 0.11 |
| Transformed Cells | | | |

TABLE-continued

Immunoreactivity Of Human Uracil DNA Glycosylases With Monoclonal Antibodies

| UDG Source | $A_{405}/A_{405\text{-}CRL\ 1222}$ | | |
|---|---|---|---|
| | 37.04.12 | 42.08.07 | 40.10.09 |
| SV-40 transformed lung fibroblasts (CCL 75.1) | 0.92 ± 0.14 | 1.12 ± 0.12 | 1.14 ± 0.21 |
| *Bloom's Syndrome Fibroblasts* | | | |
| GM 1492 | 1.02 ± 0.12 | 1.15 ± 0.07 | 0.00 |
| GM 2548 | 1.08 ± 0.09 | 1.11 ± 0.08 | 0.00 |
| GM 3402 | 1.01 ± 0.03 | 1.13 ± 0.03 | 0.00 |
| GM 3498 | 0.99 ± 0.05 | 0.94 ± 0.10 | 0.00 |
| GM 3510 | 0.81 ± 0.05 | 1.23 ± 0.22 | 0.00 |
| *Ataxia Telangiectasia Fibroblasts* | | | |
| GM 0367 | 1.17 ± 0.23 | 0.91 ± 0.24 | 0.94 ± 0.18 |
| GM 2052 | 0.85 ± 0.22 | 0.96 ± 0.08 | 1.03 ± 0.19 |
| *Xeroderma Pigmentosum Fibroblasts* | | | |
| CRL 158 | 0.98 ± 0.07 | 1.08 ± 0.20 | 0.81 ± 0.09 |
| CRL 1258 | 1.11 ± 0.25 | 0.93 ± 0.05 | 0.93 ± 0.04 |
| GM 3614 | 0.82 ± 0.04 | 0.84 ± 0.04 | 0.99 ± 0.04 |
| *Tay-Sachs Fibroblasts* | | | |
| GM 2968 | 1.20 ± 0.25 | 1.00 ± 0.06 | 0.98 ± 0.24 |
| GM 4863 | 0.80 ± 0.08 | 1.07 ± 0.08 | 0.99 ± 0.18 |
| *Familia Hypercholesterolemia Fibroblasts* | | | |
| GM 1355 | 1.07 ± 0.15 | 1.01 ± 0.08 | 1.04 ± 0.30 |
| GM 2408 | 0.65 ± 0.13 | 1.09 ± 0.06 | 0.75 ± 0.13 |
| *Galactosemia Fibroblasts* | | | |
| GM 1209 | 0.89 ± 0.13 | 0.89 ± 0.19 | 1.16 ± 0.08 |
| GM 1908 | 1.09 ± 0.13 | 1.05 ± 0.07 | 1.10 ± 0.26 |
| *Progeroid Fibroblasts* | | | |
| AG 3911** | 0.99 ± 0.09 | 0.98 ± 0.09 | 1.08 ± 0.17 |
| AG 6917 | 1.03 ± 0.12 | 1.14 ± 0.07 | 1.01 ± 0.06 |

*ATCC, Rockville, MD
**Human Genetic Cell Repository, Camden, NJ

The method of the present invention may be practiced in kit form. One such form of kit is described in U.S. Pat. No. 4,465,776. According to U.S. Pat. No. 4,465,776, a carrier is compartmentalized to receive one or more containers, such as vials or test tubes, in close confinement. A first container may contain a first monoclonal antibody such as antibody 40.10.09 which recognizes normal UDG but does not recognize Bloom's syndrome UDG. A second container may contain a second monoclonal antibody such as antibody 42.08.07 which recognizes both normal and Bloom's syndrone UDG. The first and second monoclonal antibodies may be detectably labeled, for example, by a radio or enzyme label. When an enzyme label is employed, another container in the kit may contain a suitable enzyme substrate. The monoclonal antibodies or the UDG antigen may be covalently linked to the inside of the containers.

In lieu of having the first and second monoclonal antibodies in labelled form, said antibodies may be present in unlabelled form. The kit would then alternatively include a third container of a detectably-labelled secondary antibody or F(ab) fragment which is capable of binding either the first or second UDG-specific monoclonal antibodies, e.g., sheep-, rabbit- or goat-anti-mouse IgG conjugated to alkaline phosphatase. The double antibody technique utilizing a labelled secondary antibody or F(ab) fragment is preferred since it eliminates the need for separately labeling the first and second monoclonal antibodies.

The kit may optionally include a fourth container of purified normal UDG as a positive control to test the functional integrity of the UDG-specific monoclonal antibodies.

The kit may further contain appropriate washing, dilution, and enzyme-substrate buffers.

The present invention may be embodied in other specific forms without departing from the spirit or essential attributes thereof and, accordingly, reference should be made to the appended claims, rather than to the foregoing specification, as indicating the scope of the invention.

I claim:

1. A method for diagnosing Bloom's syndrome comprising:
   contacting a human UDG-containing sample with a first anti-human UDG monoclonal antibody which does not recognize Bloom's syndrome UDG; and
   assaying said sample for binding of UDG by said monoclonal antibody.

2. A method according to claim 1 including the further step of contacting said sample with a second anti-human UDG monoclonal antibody which recognizes both normal UDG and Bloom's syndrome UDG as a control, and assaying said sample for the binding of UDG by said second monoclonal antibody.

3. A method of according to claim 2 comprising the further control step of contacting said first monoclonal antibody with normal UDG and assaying for binding of said normal UDG by said antibody to ensure the functional integrity of said first monoclonal antibody.

4. A method according to claim 1 wherein assaying comprises an enzyme-linked immunosorbent assay.

5. A method according to claim 4 wherein the monoclonal antibody is a mouse monoclonal antibody.

6. A method according to claim 5 wherein assaying binding of UDG by said first monoclonal antibody is by means of a detectably labelled anti-mouse Ig antibody.

7. A method according to claim 6 wherein alkaline phosphatase is conjugated to said anti-mouse Ig antibody as the detectable label.

8. A method according to any of claims 1, 2, 4 and 6 wherein the monoclonal antibody is ATCC HB-9311.

9. A method according to claim 2 wherein said second monoclonal antibody is selected from the group consisting of ATCC HB-9312 and ATCC HB-9313.

10. A kit for the diagnosis of Bloom's syndrome comprising:
    a carrier for receiving one or more container means;
    a first container means comprising a first detectably-labelled anti-human UDG monoclonal antibody which does not recognize Bloom's syndrome UDG; and
    a second container means comprising as a control a detectably-labelled anti-human monoclonal antibody which recognizes both normal UDG and Bloom's syndrome UDG.

11. A kit for the diagnosis of Bloom's syndrome comprising:
    a carrier for receiving one or more container means;
    a first container means comprising a first anti-human UDG monoclonal antibody which does not recognize Bloom's syndrome UDG;
    a second container means comprising as a control a second anti-human UDG monoclonal antibody which recognizes both normal UDG and Bloom's syndrome UDG; and
    a third container means comprising a detectably-labelled secondary antibody or F(ab) fragment capable of binding the first or second monoclonal antibodies.

12. A kit according to claim 10 or 11 wherein said antibodies are detectably-labelled with an enzyme label.

13. A kit according to claim 12 wherein said enzyme label is alkaline phosphatase.

14. A kit according to claim 10 or 11 wherein the first monoclonal antibody in said first compartment means is ATCC HB-9311.

15. A kit according to claim 14 wherein the monoclonal antibody in said second compartment means is selected from the group consisting of ATCC HB-9312 and ATCC HB-9313.

16. A kit according to claim 10 or 11 including an additional container means comprising purified normal UDG.

* * * * *

UNITED STATES PATENT AND TRADEMARK OFFICE
CERTIFICATE OF CORRECTION

PATENT NO. : 4,818,685

DATED : April 4, 1989

INVENTOR(S) : Michael A. Sirover

It is certified that error appears in the above-identified patent and that said Letters Patent is hereby corrected as shown below:

On Drawing Sheet 3 of 4, rotate drawing 180 degrees so that "Figure 3" appears along the right margin. (as shown on the attached sheet)

Column 2, line 63, change "or" to --of--.

Column 3, line 63-64, change "alternation" to --alteration--.

Column 5, line 6, change "radio-labes" to --radio-labels--.

Column 7, line 22, change "sodium" to --medium--.

Column 7, line 57, change "in" to --to--.

Column 9, line 12, change "4756-3761" to --3756-3761--.

Column 12, line 25, delete "of".

Signed and Sealed this

Thirteenth Day of February, 1990

Attest:

JEFFREY M. SAMUELS

Attesting Officer     Acting Commissioner of Patents and Trademarks